United States Patent

(12) United States Patent
Feller et al.

(10) Patent No.: US 8,965,737 B2
(45) Date of Patent: Feb. 24, 2015

(54) ULTRASENSITIVE BIOLOGICAL AND CHEMICAL DETECTION USING SURFACE PLASMON RESONANCE

(75) Inventors: Robert E. Feller, Los Gatos, CA (US); Andre Knoesen, Davis, CA (US); Robert D. Miller, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 649 days.

(21) Appl. No.: 13/284,025

(22) Filed: Oct. 28, 2011

(65) Prior Publication Data

US 2013/0110467 A1 May 2, 2013

(51) Int. Cl.
*G01N 21/00* (2006.01)
*G01N 21/05* (2006.01)
*G01N 21/552* (2014.01)
*G01N 21/27* (2006.01)

(52) U.S. Cl.
CPC .............. *G01N 21/05* (2013.01); *G01N 21/553* (2013.01); *G01N 21/274* (2013.01)
USPC ......................................... 702/191; 356/445

(58) Field of Classification Search
CPC ...................................................... G01N 21/05
USPC ....................................................... 702/191
See application file for complete search history.

(56) References Cited

U.S. PATENT DOCUMENTS

| | | | |
|---|---|---|---|
| 5,485,277 A | * | 1/1996 | Foster ........................... 356/445 |
| 5,822,073 A | * | 10/1998 | Yee et al. ....................... 356/445 |
| 6,784,999 B1 | | 8/2004 | Tao et al. |
| 6,943,887 B2 | | 9/2005 | Quinn et al. |
| 7,407,817 B2 | | 8/2008 | Ho et al. |
| 7,623,246 B2 | | 11/2009 | Ho et al. |
| 7,679,749 B2 | | 3/2010 | Lin et al. |

(Continued)

FOREIGN PATENT DOCUMENTS

| | | |
|---|---|---|
| EP | 2087343 | 3/2010 |
| JP | 2002337467 | 6/2004 |
| JP | 2005338475 | 6/2007 |

OTHER PUBLICATIONS

Li et al., Differential-Phase Surface Plasmon Resonance Biosensor, Analytical Chemistry, vol. 80, No. 14, Jul. 15, 2008, pp. 5590-5595.

(Continued)

*Primary Examiner* — Bryan Bui
(74) *Attorney, Agent, or Firm* — Schmeiser, Olsen & Watts, LLP

(57) ABSTRACT

A device, including sample and reference channels through which first and second solutions flow, respectively, the first solution including an analyte, the channels having a metal film in contact with the first and second solutions, the metal film configured with a linker to selectively bind the analyte; a light source whose output is modulated by an optical system, so that light is directed from the optical system alternately towards the sample and reference channels, surface plasmons within the metal film being created; a first photodetector that monitors the strength of the output from the light source; a second photodetector that collects optical signals reflected from the metal film; electronics that monitors output from the first and the second photodetectors, thereby detecting a noise-compensated difference in signals from the two channels; and a computer processor that determines, from analysis of the noise-compensated difference, presence of the analyte in the first solution.

20 Claims, 8 Drawing Sheets

(56) References Cited

U.S. PATENT DOCUMENTS

| | | |
|---|---|---|
| 7,892,855 B2 | 2/2011 | Ho et al. |
| 7,920,267 B2 | 4/2011 | Cho et al. |
| 7,933,019 B2 | 4/2011 | Chung et al. |
| 7,943,092 B2 | 5/2011 | Xiao et al. |

OTHER PUBLICATIONS

Liss et al., An Aptamer-Based Quartz Crystal Protein Biosensor, Analytical Chemistry, vol. 74, No. 17, Sep. 1, 2002, pp. 4488-4495.

McDonald et al., Fabrication of microfluidic systems in poly(dimethylsiloxane), Electrophoresis 2000, 21 (1), pages 27-40.

Ostroff et al., Fixed polarizer ellipsometry for simple and sensitive detection of thin films generated by specific molecular interactions: applications in immunoassays and DNA sequence detection, Clinical Chemistry 44:9, 1998, pp. 2031-2035.

Challener et al., A surface plasmon resonance gas sensor in a 'compact disc' format, Elsevier, Sensors and Actuators B 56 (1999) pp. 254-258.

Sun et al., Surface plasmon resonance sensor based on polarization interferometry and angle modulation, May 1, 2006, vol. 45, No. 13, Applied Optics, pp. 3071-3076.

Wu et al., Highly sensitive differential phase-sensitive surface plasmon resonance biosensor based on the Mach-Zehnder configuration, Optics Letters, vol. 29, No. 20, Oct. 15, 2004, pp. 2378-2380.

Philip C. D. Hobbs, Shot Noise Limited Optical Measurements at Baseband with Noisy Lasers, SPIE Laser Noise, vol. 1376, 1990, pp. 216-221.

Wolfgang Knoll, Interfaces and thin films as seen by bound electromagnetic waves, Annual Review of Physical Chemistry, 1998, 49: pp. 569-638.

\* cited by examiner

ULTRASENSITIVE BIOLOGICAL AND CHEMICAL DETECTION USING SURFACE PLASMON RESONANCE

This invention was made with government support under ECCS-0823827 awarded by the National Science Foundation. The government has certain rights in the invention.

FIELD OF THE INVENTION

The present invention relates to a method of optical sensing, and an associated apparatus, using surface plasmon resonance (SPR) to achieve ultrasensitive interfacial detection of gas and solution-phase biological and chemical analytes.

BACKGROUND OF THE INVENTION

Biosensors directed towards disease and cancer detection often target biomarkers such as proteins that are not present in healthy individuals. The buildup of these biomarkers correlates with the progression of the particular disease. Unfortunately, the number of available treatment options and the overall prognosis decrease considerably as the disease progresses from early to advanced stages. Further, many diseases are asymptomatic until the advanced stages, at which point options are limited. For these reasons, early detection is critical for successful treatment.

The gold standard for biosensing has been ELISA (enzyme-linked immunosorbent assay), which is utilized in commercial products such as pregnancy tests, as well as for detection of antibiotics in milk and the presence of salmonella. Similarly, sandwich assays can be performed with fluorescently-labeled secondary antibodies. In both cases, however, antibody labeling is a requirement. While these labeled methods typically provide adequate signal-to-noise ratio, the production of labeled antibodies is expensive, time consuming, and can influence molecular binding. Further, since the sandwich assay requires multiple incubation steps, these assays do not permit real-time detection.

Many techniques have been developed to overcome the shortcomings of bio sensors that require molecular labeling. These techniques typically probe the interfacial binding of a particular protein by means of changes in interfacial refractive index or mass. Surface plasmon resonance (Knoll, W., Interfaces and thin films as seen by bound electromagnetic waves, *Annual review of physical chemistry* 1998, 49 (1), 569-638) and ellipsometry (Ostroff, R. M.; Maul, D.; Bogart, G. R.; Yang, S.; Christian, J.; Hopkins, D.; Clark, D.; Trotter, B.; Moddel, G., Fixed polarizer ellipsometry for simple and sensitive detection of thin films generated by specific molecular interactions: applications in immunoassays and DNA sequence detection, *Clin Chem* 1998, 44 (9), 2031-2035) are common techniques for monitoring interfacial refractive index, while quartz crystal microbalance (Liss, M.; Petersen, B.; Wolf, H.; Prohaska, E., An Aptamer-Based Quartz Crystal Protein Biosensor, *Analytical chemistry* 2002, 74 (17), 4488-4495) measures interfacial mass change. A number of different modifications have been proposed to reduce the noise in surface plasmon resonance (SPR) sensors such as polarization interferometry (Sun, Z. L.; He, Y. H.; Guo, J. H., Surface plasmon resonance sensor based on polarization interferometry and angle modulation, *Applied Optics* 2006, 45 (13), 3071-3076) and differential phase change (Wu, S.; Ho, H.; Law, W.; Lin, C.; Kong, S., Highly sensitive differential phase-sensitive surface plasmon resonance biosensor based on the Mach-Zehnder configuration, *Optics letters* 2004, 29 (20), 2378-2380). A very low (or possibly the lowest known) detection limit for SPR based biosensing has been demonstrated by Li et al. (Li, Y. C.; Chang, Y. F.; Su, L. C.; Chou, C., Differential-phase surface plasmon resonance biosensor, *Analytical chemistry* 2008, 80 (14), 5590-5595). Li et al. use differential-phase-sensitive surface plasmon resonance to monitor the interaction between mouse IgG and antimouse IgG at 67 attomolar concentration. While this is an impressive achievement, there are a number of disadvantages with the experimental setup of Li et al. One important disadvantage relates to the sensitivity of the apparatus. It is well known that for phase-sensitive SPR measurements, the largest sensitivity to phase change occurs at the minimum angle of reflectivity. However, operating at minimum reflection where only a small percentage of photons reach the detector severely reduces the signal-to-noise ratio. Operating outside of the minimum reflection or changing the gold thickness can increase reflectivity but only at the expense of the phase sensitivity. Increasing laser power is also not a viable option, since the adsorbed photons dissipate as heat in the dielectric material of interest and at high powers can create temperature gradients in the sample. Further, phase measurements are sensitive to the roughness of the gold film. Achieving ultrasmooth gold films and substrates for gold deposition can be a daunting task that is required for this configuration to maintain the optimum sensitivity. In addition, there is an extremely narrow dynamic range for phase detection. Thus, only extremely low interfacial concentrations or smaller molecules can be measured. For real-world applications, such as detection in serum, non-specific adsorption alone would likely cause departure from the usable detection range.

SUMMARY OF THE INVENTION

The present invention provides a device, comprising:

sample and reference channels through which first and second solutions flow, respectively, wherein the first solution includes an analyte of interest, the channels having a metal film in contact with the first and second solutions, a surface of the metal film configured with a linker to selectively bind the analyte to the surface of the metal film;

a light source whose output is modulated by an optical system, so that light is directed from the optical system alternately towards the sample and reference channels, wherein surface plasmons within the metal film are created;

a first photodetector that monitors the strength of the output from the light source;

a second photodetector that collects optical signals reflected from the metal film;

electronics that monitors output from both the first and the second photodetectors, thereby detecting a noise-compensated difference in signals from the two channels; and a computer processor that determines, from analysis of the noise-compensated difference, that the analyte is present in the first solution.

The present invention provides an apparatus for detecting an analyte, said apparatus comprising:

a reference channel through which a reference fluid is flowing;

a sample channel through which a sample fluid is flowing, said sample fluid comprising the reference fluid and the analyte, said reference fluid comprising a molar concentration of the analyte that is no more than 50% of the analyte that is in the sample fluid, said reference channel and said sample channel being different channels;

a metal layer in contact with the sample fluid and the reference fluid, a surface of the metal layer configured with a linker to selectively bind the analyte to the surface of the metal layer;

an optical system;

a reference photodetector coupled to the optical system;

a sample photodetector;

noise reduction electronics coupled to the reference photodetector and the sample photodetector;

a lock-in amplifier coupled to the noise reduction electronics; and a computer processor coupled to the lock-in amplifier;

said optical system configured to receive a scanning beam from a laser, said scanning beam comprising laser noise generated in the laser;

said optical system configured to split the scanning beam into a reference beam and a sample beam, said sample beam and said reference beam each comprising the laser noise;

said optical system configured to direct the reference beam to the reference photodetector causing the reference photodetector to send a resultant reference signal containing the laser noise to the noise reduction electronics;

said optical system configured to direct the sample beam alternately toward the sample channel and the reference channel under conditions where surface plasmon resonance (SPR) occurs in the metal layer, said directed sample beam being alternately reflected from the surface of the metal layer at the sample and reference channels;

said optical system configured to direct the reflected sample beam to the sample photodetector causing the sample photodetector to send a resultant sample signal containing the laser noise to the noise reduction electronics;

said noise reduction electronics configured to (i) implement a reduction of the laser noise from the sample signal via utilization of the reference signal and (ii) generate an output signal comprising the sample signal after the laser noise has been removed from the sample signal;

said lock-in amplifier configured to (i) lock in to the output signal from the noise reduction electronics and (ii) determine, from processing different portions of cycles of the output signal from the noise reduction electronics, a difference in amplitude ($\Delta A$) between the alternately directed beams reflected at the metal layer, said $\Delta A$ being determined after the laser noise has been cancelled from the sample signal;

said computer processor configured to determine, from analysis of the difference in amplitude ($\Delta A$) determined by the lock-in amplifier, that the analyte is present in the sample fluid flowing in the sample channel.

The method of optical sensing, and an associated apparatus, of the present invention offers the advantage of being both label-free (e.g., free of fluorescent tags) and having considerably lower baseline noise than alternative label-free techniques. Since detection is directly related to the signal to noise ratio, reduction of the noise floor increases precision and can be used to achieve detection at the lower concentrations present during early stages of disease. Further, the method and apparatus of the present invention can be used in a unique self-referencing configuration to eliminate the undesired contribution of non-specific interfacial adsorption (e.g., serum proteins), making the apparatus particularly useful for ultra-sensitive measurements in the presence of complex media (e.g., blood).

DETAILED DESCRIPTION OF THE INVENTION

Figure 1A:
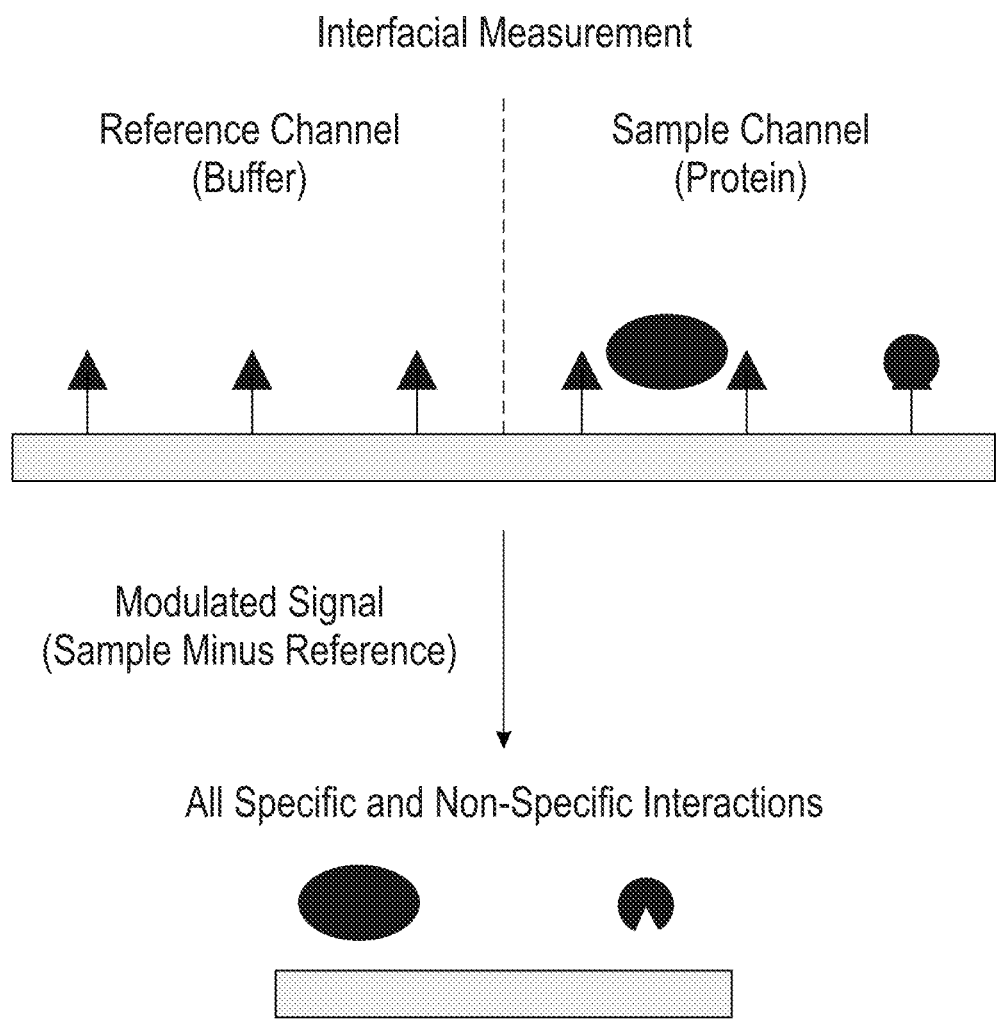
FIG. 1A depicts all specific and non-specific interactions from an interfacial measurement using a surface plasmon resonance (SPR) sensor with modulation, in accordance with embodiments of the present invention.

The present invention uses surface plasmon resonance (SPR) to monitor the reflected intensity with modulation to achieve the shot-noise detection limit. However, unlike phase detection which operates at the minimum reflection angle, the present invention uses intensity measurements that are most sensitive away from the minimum reflection angle, which increases the achievable signal-to-noise ratio while not heating the sample considerably. To understand why modulation is used, the reduction of noise through modulation and how to implement modulation in the present invention are discussed next.

In general, the detection limit of a specific analyte is determined by the biosensor's sensitivity and noise. The biosensor's sensitivity is related to the change in interfacial refractive index which depends upon analyte binding and which results in a change in reflected beam intensity (see FIG. 7, discussed infra). For intensity measurements using surface plasmon resonance signal, the sensitivity depends on the excitation wavelength and interfacial architecture. The presence of the analyte is monitored by the change in output signal relative to the system noise. Since the sensitivity to analyte is predetermined, improvement in detection is accomplished by the reduction of noise.

For surface plasmon resonance, laser noise (defined as noise in excess of the shot noise, spurious modulation, and power drift) is the major source of noise. The amplitude of the laser noise is less at higher frequencies. Therefore, the present invention implements splitting a laser beam into a sample beam and a reference beam to significantly reduce laser noise.

Shot noise is the fundamental noise limit as determined by photon statistics and is the theoretical quantum noise for the emitted light power from the laser. Achieving the shot-noise limited detection may be realized by compensating for the sources of laser noise or operating at a frequency where laser noise levels are minimal compared to shot noise. Unfortunately, the latter requires operating frequencies from one to several hundred megahertz depending on the laser source, which is not readily achievable.

The method described herein of shot-noise limited surface plasmon resonance-based detection is accomplished by spatially manipulating the laser beam to rapidly switch between a reference channel (which remains fixed with time) and a sample channel (where the interfacial biochemical reaction or adsorption of interest occurs). In addition, a photodetector is used to achieve the shot-noise limited detection by compensating for the sources of laser noise or operating at a frequency where laser noise levels are minimal compared to shot noise. The photodetector uses an all-electronic noise reduction scheme which subtracts a photocurrent associated with the reference beam from a photocurrent associated with the sample beam. Furthermore, for the photodetector to suppress laser noise, the intensity on the photodetector must not deviate during the transition between the channels as would occur with beam chopping. The present invention provides a first embodiment and a second embodiment for spatial beam manipulation in a manner that permits the use of balanced photodetection to achieve the fundamental shot-noise detection limit.

Further, this modulation configuration provides a unique characteristic relative to standard labeled or label-free sensors. This modulation scheme has the inherent advantage of being entirely self-referencing in one embodiment by having the modulation itself reference out (i.e., remove from consideration) non-specific adsorption (e.g., adsorption of a background protein) and generate a signal for only an analyte of interest (e.g., a protein of interest). Therefore, while non-specific adsorption is often a problem for standard interfacial detection, which limits commercial viability, modulation according to the present invention examines differences between signals alternately reflected from sample and reference channels and could isolate specific recognition in the presence of non-specific adsorption. As described above, one channel (i.e., the reference channel) remains unchanged throughout implementation of the methods of the present invention. In the modulated system, the reference channel requires a buffer flow (see FIG. 1A) since the modulated signal continuously examines the difference between the sample and reference channels.

FIG. 1A depicts all specific and non-specific interactions from an interfacial measurement using a SPR sensor with modulation, in accordance with embodiments of the present invention. Thus in FIG. 1A, the modulated signal, which is alternately directed toward the sample channel and the reference channel at a frequency of alternation (i.e., modulation frequency), represents all interfacial interactions, both specific and non-specific.

Figure 1B:
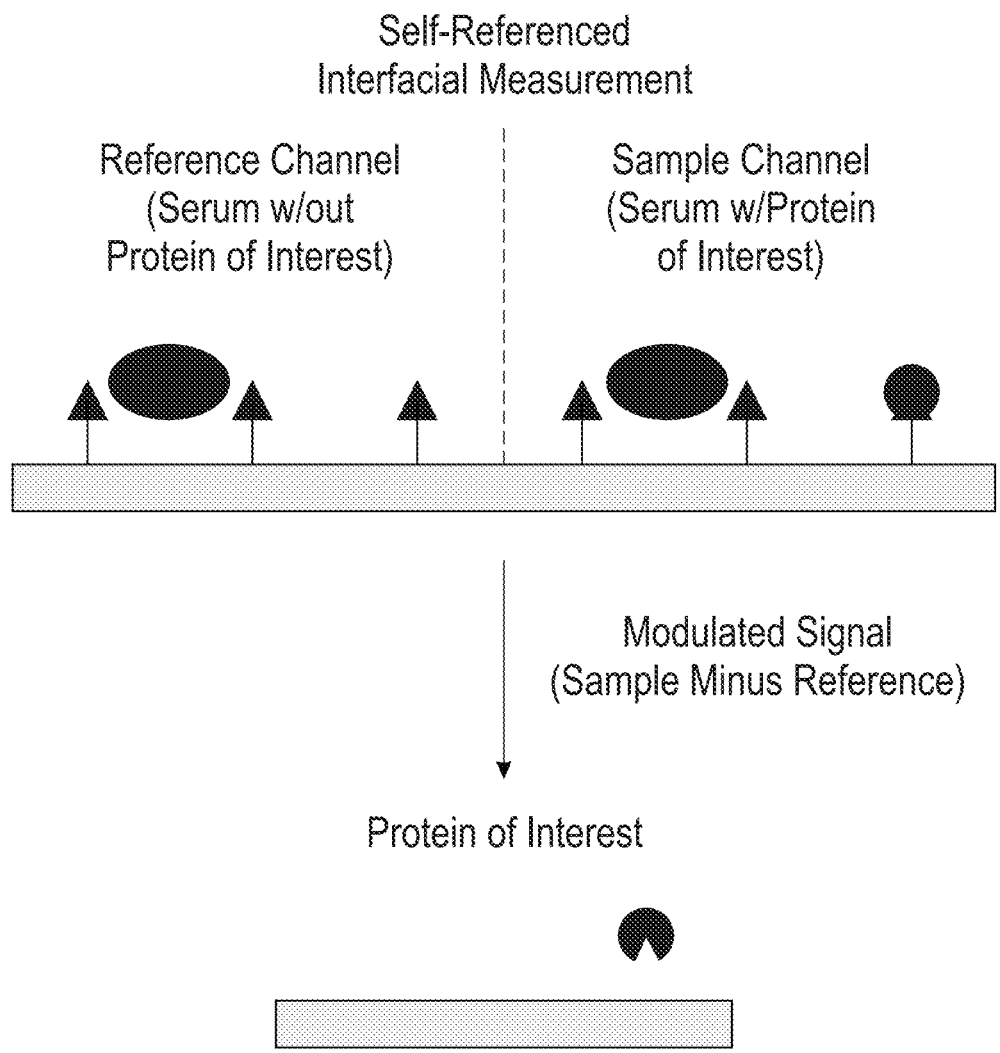
FIG. 1B depicts a protein of interest from a self-referenced interfacial measurement using a SPR sensor with modulation, in accordance with embodiments of the present invention.

FIG. 1B depicts a protein of interest from a self-referenced interfacial measurement using a SPR sensor with modulation, in accordance with embodiments of the present invention. Thus in FIG. 1B, the background protein is present in both the reference channel and the sample channel, and the protein of interest is present in only the sample channel. Thus, the non-specific adsorption is referenced out by the modulation, and a signal is generated by the protein of interest in one embodiment. A sensor that utilizes a specific interaction (aptamer or antibody) upstream of the reference measurement may be employed to filter the protein of interest from the reference channel to test for the presence of a specific biomarker.

A first embodiment and a second embodiment of the present invention for increasing the sensitivity of surface plasmon resonance are described infra. Surface plasmon polaritons are electromagnetic waves confined to the interface between a metal and a dielectric. The intensity of these electromagnetic waves decays exponentially into the bulk medium of the metal making the electromagnetic waves exquisitely sensitive to change in refractive index of the interface between the metal and the dielectric. Surface plasmon resonance is an optical technique that utilizes surface plasmon polaritons to monitor small changes occurring at the interface such as the adsorption or desorption of proteins.

First Embodiment

Figure 2A:
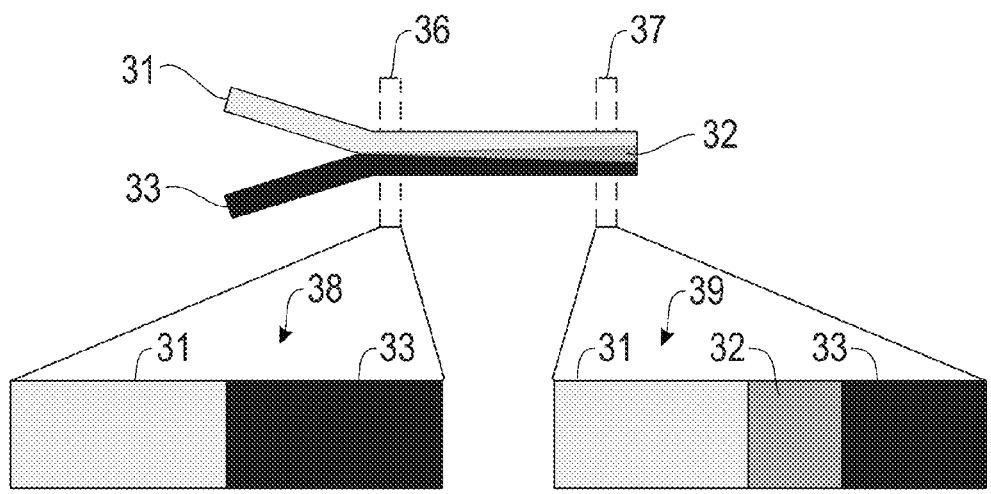
FIG. 2A depicts adjacent streams within a single channel of a fluid cell at an initial time and a later time, in accordance with embodiments of the present invention.

FIG. 2A depicts adjacent streams 31 and 33 within a single channel of a fluid cell at a first position 36 corresponding to an initial time and a second position 37 corresponding to a later time, in accordance with embodiments of the present invention. At the first position 36, the adjacent streams 31 and 33 are separate streams because insufficient time has elapsed for mixing of the streams to occur, as depicted in the projection 38 of the adjacent streams 31 and 33. At the second position 37, a mixed fluid region 32 has formed between the adjacent streams 31 and 33 due to turbulent mixing of the adjacent streams 31 and 33, as depicted in the projection 39 of the streams 31, 32, and 33.

Figure 2B:
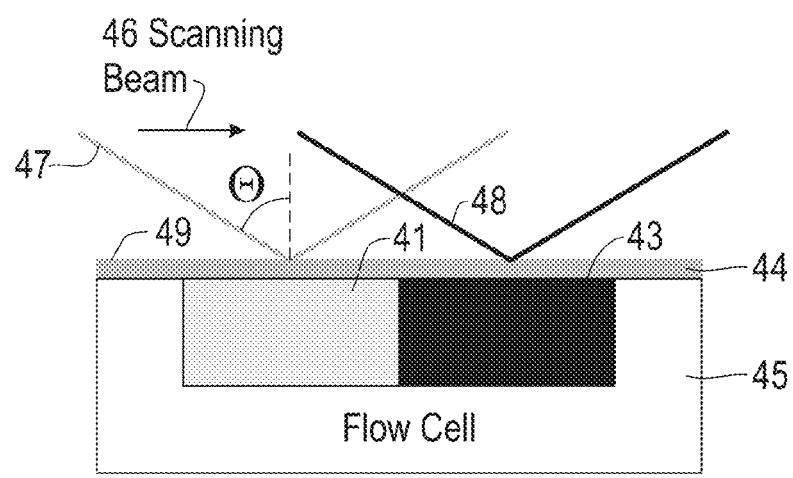
FIG. 2B depicts adjacent streams within a flow cell, in accordance with embodiments of the present invention.

FIG. 2B depicts adjacent streams 41 and 43 within a flow cell 45, in accordance with embodiments of the present invention. The flow cell 45 has channel dimensions for achieving a low Reynolds number that produces laminar flow (i.e., flow having a Reynold's number less than 2000) under which fluid mixing occurs by diffusion rather than by the convection that characterizes the standard turbulent flow illustrated in FIG. 2A. Therefore since diffusion is relatively slow, the adjacent streams 41 and 43 must travel a considerable distance before a mixed fluid region can form.

FIG. 2B also depicts a metal film (e.g., a gold film) 44 on which reflects a scanning beam 46. The metal film 44 is on adjacent streams 41 and 43. Most of the light from the scanning beam 46 is reflected, except under a condition of surface plasmon resonance in which the light from the scanning beam 46 is essentially totally absorbed into the metal film 44 and may be subsequently detected as a signal of decreased energy as compared with the energy of the reflected beam under conditions in which surface plasmon resonance is absent. The scanning beam 46 is depicted as beams 47 and 48 which alternate between streams 41 and 43 at a frequency of alternation. This alternation is a modulation which may be used to eliminate or substantially reduce noise from a laser that generates the scanning beam 46.

Figure 3A:
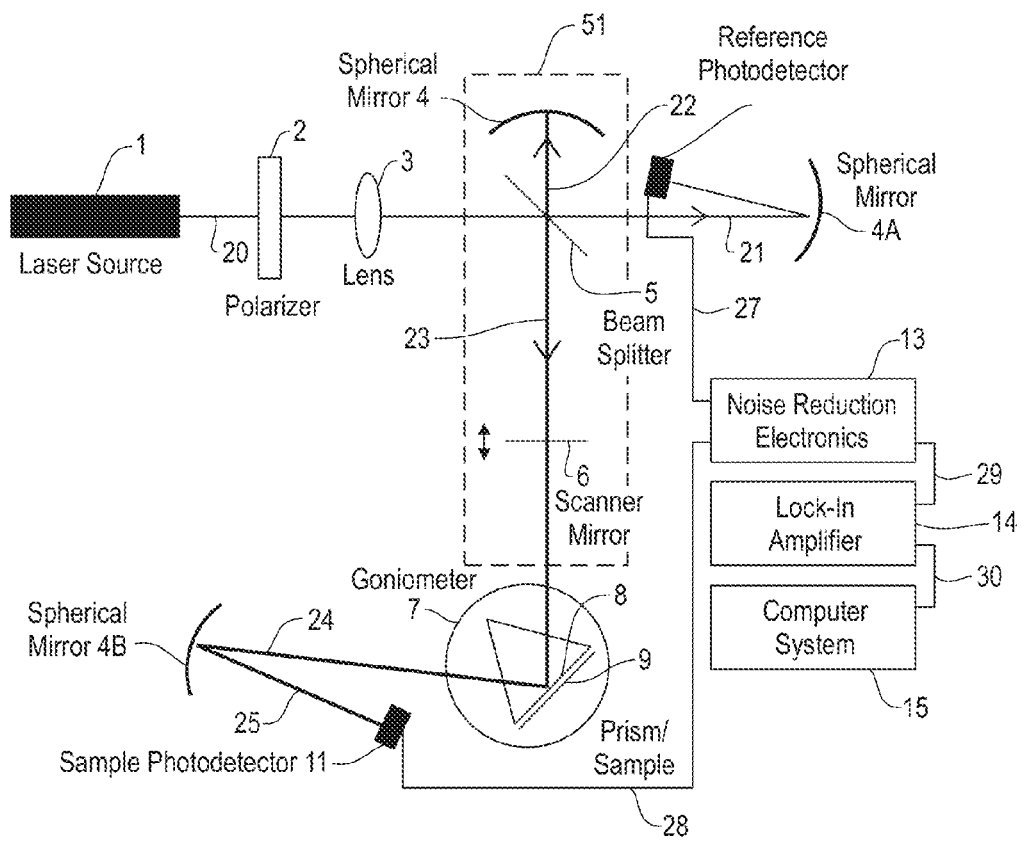
FIG. 3A depicts a top view of an apparatus or device comprising an optical system that includes a scanning mirror for alternately directing a scanning beam from a laser onto a sample channel and a reference channel of a flow cell, in accordance with embodiments of the present invention.
Figure 3B:
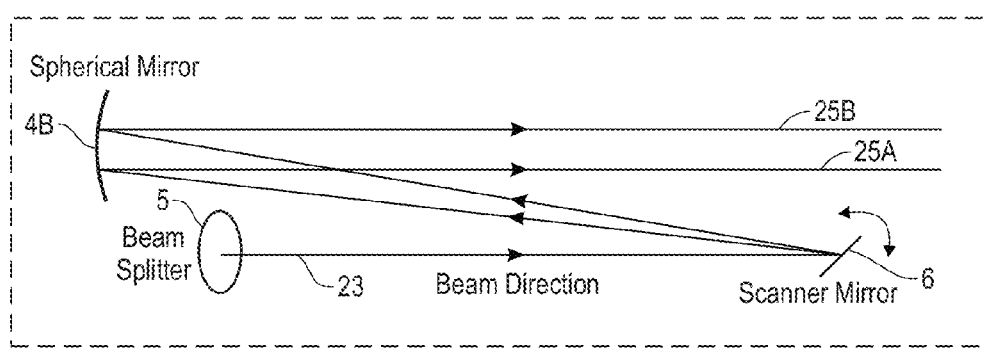
FIG. 3B depicts a vertical cross section of the optical system of FIG. 3A, in accordance with embodiments of the present invention.

The first embodiment of the present invention, as illustrated in FIGS. 3A and 3B described infra, utilizes a scanning mirror in combination with a single flow cell to rapidly sweep a scanning beam between the reference and sample channels within the flow cell. The flow cell provides a seamless transition in refractive index while still maintaining distinctly isolated channels. If these channels were physically separated by a barrier, the refractive index difference between the barrier and the buffer solution would produce a considerable change in signal intensity. Similar to beam chopping, the intensity change resulting from this refractive index difference causes a considerable deterioration in the noise suppression. For typical flow cells, removing the barrier leads to turbulent mixing of the solutions. However, using a barrierless flow cell with the appropriate channel dimensions to achieve a low Reynolds number of less than 2000, produces laminar flow. Under laminar flow constraints of the Reynold's number being less than 2000, fluid mixing occurs via diffusion rather than via convection as with the standard turbulent flow illustrated in FIG. 2A. Therefore, adjacent streams within a single channel can travel a considerable distance before interfacial mixing occurs, thus eliminating the need for a physical barrier that would change the refractive index between the channels. A reflected beam can pass across the solution interface without signal disruption created by a barrier, which will allow the system noise to achieve shot-noise limited detection. One of the primary benefits is that this noise suppression scheme can be realized without complex modifications to the original surface plasmon resonance setup. A flow cell for use with the present invention may be fabricated out of polydimethylsiloxane using standard soft lithography methodology. A scanning mirror is introduced into the beam path to oscillate the beam between the reference channel and the sample channel.

FIG. 3A depicts a top view of an apparatus or device comprising an optical system 51 that includes a scanning mirror 6 for alternately directing a scanning beam 20 from a laser 1 onto a sample channel and a reference channel of a barrierless flow cell 9, in accordance with embodiments of the present invention. In one embodiment, the fluid in the sample channel and the fluid in the reference channel are essentially separated from each other. FIG. 3B depicts a vertical cross section of the optical system 51 of FIG. 3A, in accordance with embodiments of the present invention.

The scanning beam 20 includes a laser noise component whose amplitude reflects the laser noise (i.e., noise in excess of the shot noise, spurious modulation, and power drift) generated in the laser 1. The scanning beam 20, after passing through a polarizer 2 and a lens 3, is split by a beam splitter 5 into a reference beam 21 and a sample beam 22. Both the reference beam 21 and the sample beam 22 include the laser noise component of the scanning beam 20.

The reference beam 21 is collected by a reference photodetector 10 which outputs a resultant reference signal 27 that is directed to noise reduction electronics 13. The reference signal 27 includes the laser noise component of the reference beam 21.

In one embodiment, the reference photodetector 10 is a photodiode, wherein the reference signal 27 is a photocurrent.

In one embodiment, the reference photodetector 10 is a wireless device, wherein the reference signal is a wireless signal.

The sample beam 22 is directed to a spherical mirror 4 which reflects and redirects the sample beam 22 toward a scanner mirror 6. After being redirected toward the scanner mirror 6, the sample beam is denoted by reference numeral 23.

The scanner mirror 6 engages in a rotation about its axis to direct the sample beam 23 alternately toward the sample channel and the reference channel of the flow cell 9 at a modulation frequency determined by the motion of the scanner mirror 6.

The alternately directed beams are reflected at the metal layer 8 in contact with the flow cell 9. The reflections occur alternately at the sample channel and the reference channel. The reflected beams are directed toward the spherical mirror 4B. FIG. 3B shows the reflected beams striking the spherical mirror 4B at two different elevations to make the reflected beams parallel to each other as parallel beams 25A and 25B, after which the beams 25A and 25B are collected by a sample photodetector 11 which outputs a resultant sample signal 28 that is directed to the noise reduction electronics 13. The sample signal 28 includes the same laser noise component that is included in the reference signal 27.

In one embodiment, the sample photodetector 11 is a photodiode, wherein the sample signal 28 is a photocurrent.

In one embodiment, the sample photodetector 11 is a wireless device, wherein the sample signal 28 is a wireless signal.

The noise reduction electronics 13 receives the sample signal 28 and the reference signal 27 either as: (i) photocurrents (e.g., if the sample photodetector 11 and the reference photodetector 10 are photodiodes); or (ii) electric currents into which the sample signal 28 and the reference signal 27 have been converted (e.g., if the sample photodetector 11 and the reference photodetector 10 are wireless devices). The symbols $I_{SAMP}$ and $I_{REF}$ denote the time varying electric currents associated with the sample signal 28 and the reference signal 27, respectively. The time varying electric currents $I_{SAMP}$ and $I_{REF}$ are received and processed by the noise reduction electronics 13.

The noise reduction electronics 13 generates an output signal 29, denoted as $I_{OUT}$, which comprises the sample signal 28 after the laser noise component has been removed from the sample signal 28 by being cancelled by the laser noise component of the reference signal 27.

In one embodiment, the noise reduction electronics 13 determines the output signal 29 as $I_{OUT}=I_{SAMP}-(I_{REF}-I_{REFDC})$ wherein $I_{REFDC}$ is the DC value of $I_{REF}$. The preceding determination of $I_{OUT}$ may be implemented using the electronic noise reduction scheme described in Hobbs, P. C. D., Shot Noise Limited Optical Measurements at Baseband with Noisy Lasers, *SPIE Laser Noise* 1990, 1376, 216-221.

In one embodiment, the noise reduction electronics 13 contains a feedback loop that splits the electric current $I_{REF}$ in each feedback cycle to generate a reduction current $I_{SUB}$ such that the laser noise component is identified and subsequently cancelled from $I_{SAMP}$ upon determining that the DC value of $I_{SUB}$ equals the DC value of $I_{SAMP-RC}$ (which occurs during one of the feedback cycles), wherein $I_{SAMP-RC}$ is the value of a portion of $I_{SAMP}$ corresponding to the reflected sample beam from the reference channel.

In one embodiment, the noise reduction electronics 13 may implement a determination of a ratio of $I_{SAMP}$ to $I_{REF}$ which approximately eliminates the presence of the laser noise component in the reduced-noise value of $I_{SAMP}$ that is used in the determination of $I_{OUT}$.

The electronic noise reduction scheme in the noise reduction electronics 13 enables achievement of the shot-noise limited detection of analyte in the sample channel of the flow cell 9.

The output signal 29 from the noise reduction electronics 13 is processed by a lock-in amplifier 14 that locks in (i.e., selects) the output signal 29 having the modulation frequency determined by the scanner mirror 6. Noting that the output signal 29 is periodic in accordance with the frequency of alternation (i.e., modulation frequency), the lock-in amplifier 14 determines, from processing different portions of cycles of the output signal 29, the difference in amplitude (ΔA) between the alternately directed beams reflected at metal layer 8. The difference in amplitude (ΔA) is included in the output signal 30 from the lock-in amplifier 14.

The output signal 30 from the lock-in amplifier 14 is sent to a computer system 15 for further processing by a computer processor of the computer system, which includes determining the presence and amount of analyte in the fluid of the sample channel. In one embodiment, the amount of analyte present in the fluid of the sample channel may be determined from a calibration curve that plots the difference in amplitude (ΔA) versus amount or concentration of analyte present. The calibration curve is specific to the analyte of interest being considered. In one embodiment, the maximum molar concentration of analyte that may be in the reference fluid is about 50% of that in the sample fluid.

Second Embodiment

Figure 4A:
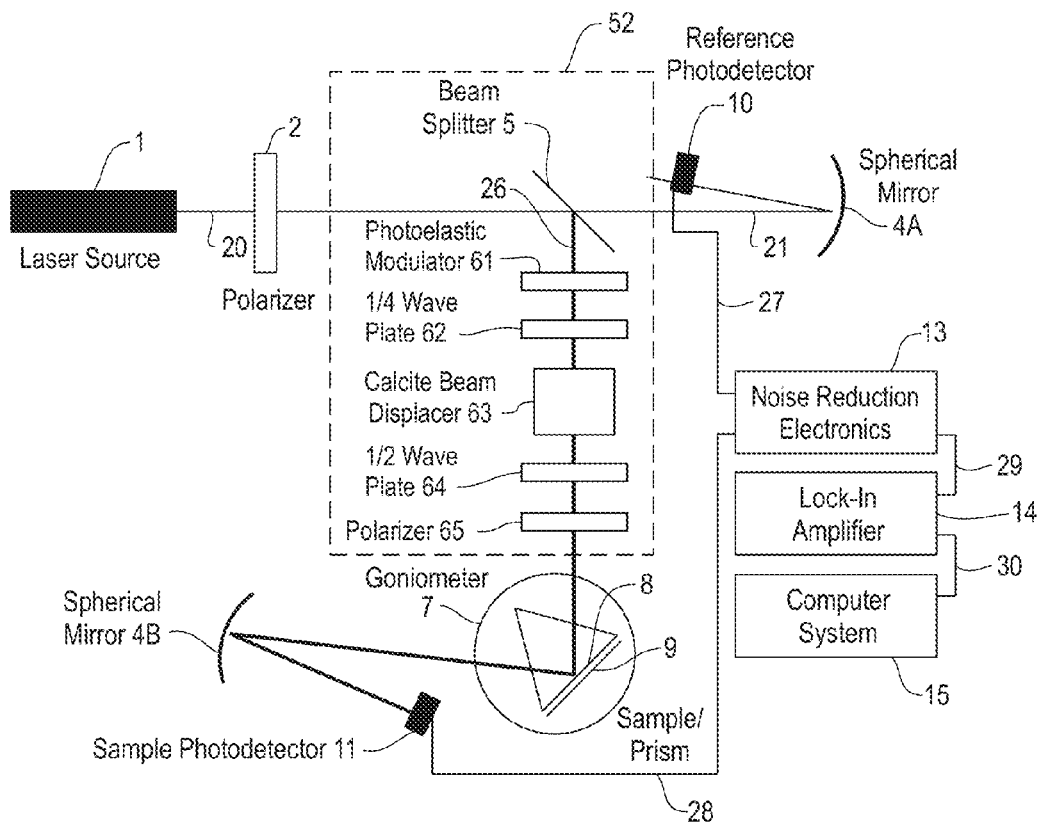
FIG. 4A depicts a top view of an apparatus or device comprising an optical system that includes a calcite beam splitter for splitting a scanning beam from a laser into beams alternately directed to a sample channel and a reference channel of a flow cell, in accordance with embodiments of the present invention.
Figure 4B:
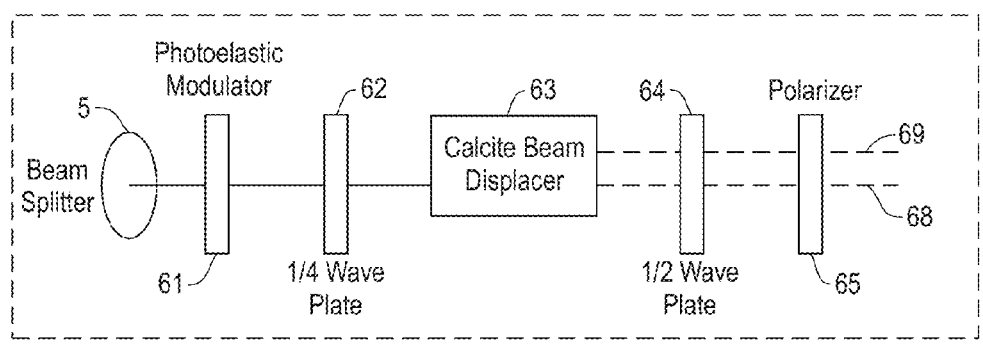
FIG. 4B depicts a vertical cross section of the optical system of FIG. 4A, in accordance with embodiments of the present invention.

FIG. 4A depicts a top view of an apparatus or device comprising an optical system 52 that includes a polarizing beam splitter 63 for alternately directing a scanning beam 20 from a laser 1 onto a sample channel and a reference channel of a flow cell 9, in accordance with embodiments of the present invention. In one embodiment, the fluid in the sample channel and the fluid in the reference channel are essentially separated from each other. FIG. 4B depicts a vertical cross section of the optical system 52 of FIG. 4A, in accordance with embodiments of the present invention.

The scanning beam 20 includes a laser noise component whose amplitude reflects the spurious noise (i.e., in excess of the shot noise) generated in the laser 1. The scanning beam 20, after passing through a polarizer 2, is split by a beam splitter 5 into a reference beam 21 and a sample beam 26. Both the reference beam 21 and the sample beam 22 include the laser noise component of the scanning beam 20.

The reference beam 21 is collected by a reference photodetector 10 which outputs a resultant reference signal 27 that is directed to a noise reduction electronics 13. The reference signal 27 includes the laser noise component of the reference beam 21.

In one embodiment, the reference photodetector 10 is a photodiode, wherein the reference signal 27 is a photocurrent.

In one embodiment, the reference photodetector 10 is a wireless device, wherein the reference signal is a wireless signal.

The sample beam 26 passes through a photoelastic modulator 61 which changes the polarization of the sample beam 26 at a specific frequency defined by the photoelastic modulator 61 to modulate (i.e., alternate) the polarization rapidly (e.g., at 50,000 Hz) between circularly polarized light and P polarized light.

After passing through the photoelastic modulator 61, the sample beam 26 passes through a quarter-wave plate 62 that changes the circularly polarized light to linearly polarized light, which results in the sample beam 26 being modulated between two polarizations, namely S polarized light and P polarized light, with respect to the reflecting SPR surface of the metal layer 8.

After passing through the quarter-wave plate 62, the sample beam 26 passes through the polarizing beam displacer (e.g., a calcite beam displacer) 63 which displaces the S and P polarizations by a distance determined by the geometry of the polarizing beam displacer 63, which generates displaced beams 68 and 69. The polarizing beam displacer 63 allows one of the two polarizations to pass directly through without being displaced and causes the other of the two polarizations to be displaced by a certain distance. Thus, the displaced beams 68 and 69 alternate back and forth between the two spatial positions as the photoelastic modulator 61 changes the polarization. Although any polarizing beam displacer would work, most polarizing beam displacers require more alignment than does the calcite beam displacer 63 which may be used for simplicity.

The two displaced beams 68 and 69 emerging from the polarizing beam splitter 63 are then rotated by 45 degrees by a half-wave plate 64 such that the overall P polarization between the two displaced beams 68 and 69 remains constant with time.

Then, a linear polarizer 65 removes the S polarization which is not needed for surface plasmon resonance, which creates a beam with constant overall intensity that alternates between two positions in space allowing for the use of two separate flow cells, said two positions corresponding to where the sample channel and the reference channel are located.

The two displaced beams 68 and 69 are reflected at metal layer 8 in contact with the flow cell 9. The reflections occur alternately at the sample channel and the reference channel. The reflected beams are directed toward the spherical mirror 4B and then striking spherical mirror 4B at two different elevations to make the two displaced beams parallel to each other as described supra in conjunction with FIG. 3B, after which the two displaced beams are collected by a sample photodetector 11 which outputs a resultant sample signal 28 that is directed to the noise reduction electronics 13. The sample signal 28 includes the same laser noise component that is included in the reference signal 27.

In one embodiment, the sample photodetector 11 is a photodiode, wherein the sample signal 28 is a photocurrent.

In one embodiment, the sample photodetector 11 is a wireless device, wherein the sample signal 28 is a wireless signal.

The noise reduction electronics 13 receives the sample signal 28 and the reference signal 27 either as: (i) photocurrents (e.g., if the sample photodetector 11 and the reference photodetector 10 are photodiodes); or (ii) electric currents into which the sample signal 28 and the reference signal 27 have been converted (e.g., if the sample photodetector 11 and the reference photodetector 10 are wireless devices). The symbols $I_{SAMP}$ and $I_{REF}$ denote the time varying electric currents associated with the sample signal 28 and the reference signal 27, respectively. The time varying electric currents $I_{SAMP}$ and $I_{REF}$ are received and processed by the noise reduction electronics 13.

The noise reduction electronics 13 generates an output signal 29, denoted as $I_{OUT}$, which comprises the sample signal 28 after the laser noise component has been removed from the sample signal 28 by being cancelled by the laser noise component of the reference signal 27.

In one embodiment, the noise reduction electronics 13 determines the output signal 29 as $I_{OUT}=I_{SAMP}-(I_{REF}-I_{REFDC})$ wherein $I_{REFDC}$ is the DC value of $I_{REF}$. The preceding determination of $I_{OUT}$ may be implemented using the electronic noise reduction scheme described in Hobbs, P. C. D., Shot Noise Limited Optical Measurements at Baseband with Noisy Lasers, *SPIE Laser Noise* 1990, 1376, 216-221.

In one embodiment, the noise reduction electronics 13 contains a feedback loop that splits the electric current $I_{REF}$ in each feedback cycle to generate a reduction current $I_{SUB}$ such that the laser noise component is identified and subsequently cancelled from $I_{SAMP}$ upon determining that the DC value of $I_{SUB}$ equals the DC value of $I_{SAMP-RC}$ (which occurs during one of the feedback cycles), wherein $I_{SAMP-RC}$ is the value of a portion of $I_{SAMP}$ corresponding to the reflected sample beam from the reference channel.

In one embodiment, the noise reduction electronics 13 may implement a determination of a ratio of $I_{SAMP}$ to $I_{REF}$ which approximately eliminates the presence of the laser noise component in the reduced-noise value of $I_{SAMP}$ that is used in the determination of $I_{OUT}$.

The electronic noise reduction scheme in the noise reduction electronics 13 enables achievement of the shot-noise limited detection of analyte in the sample channel of the flow cell 9.

The output signal 29 from the noise reduction electronics 13 is processed by a lock-in amplifier 14 that locks in (i.e., selects) the output signal 30 having the modulation frequency determined by the scanner mirror 6. Noting that the output signal 29 is periodic in accordance with the frequency of alternation (i.e., modulation frequency), the lock-in amplifier 14 determines, from processing different portions of cycles of the output signal 29, the difference in amplitude ($\Delta A$) between the alternately directed beams reflected at metal layer 8. The difference in amplitude ($\Delta A$) is included in the output signal 30 from the lock-in amplifier 14.

The output signal 30 from the lock-in amplifier 14 is sent to a computer system 15 for further processing by a computer processor of the computer system, which includes determining the presence and amount of analyte in the fluid of the sample channel. In one embodiment, the amount of analyte present in the fluid of the sample channel may be determined from a calibration curve that plots the difference in amplitude ($\Delta A$) versus amount or concentration of analyte present. The calibration curve is specific to the analyte of interest being considered. In one embodiment, the maximum molar concentration of analyte that may be in the reference fluid is about 50% of that in the sample fluid.

Inventive Method

Figure 5:
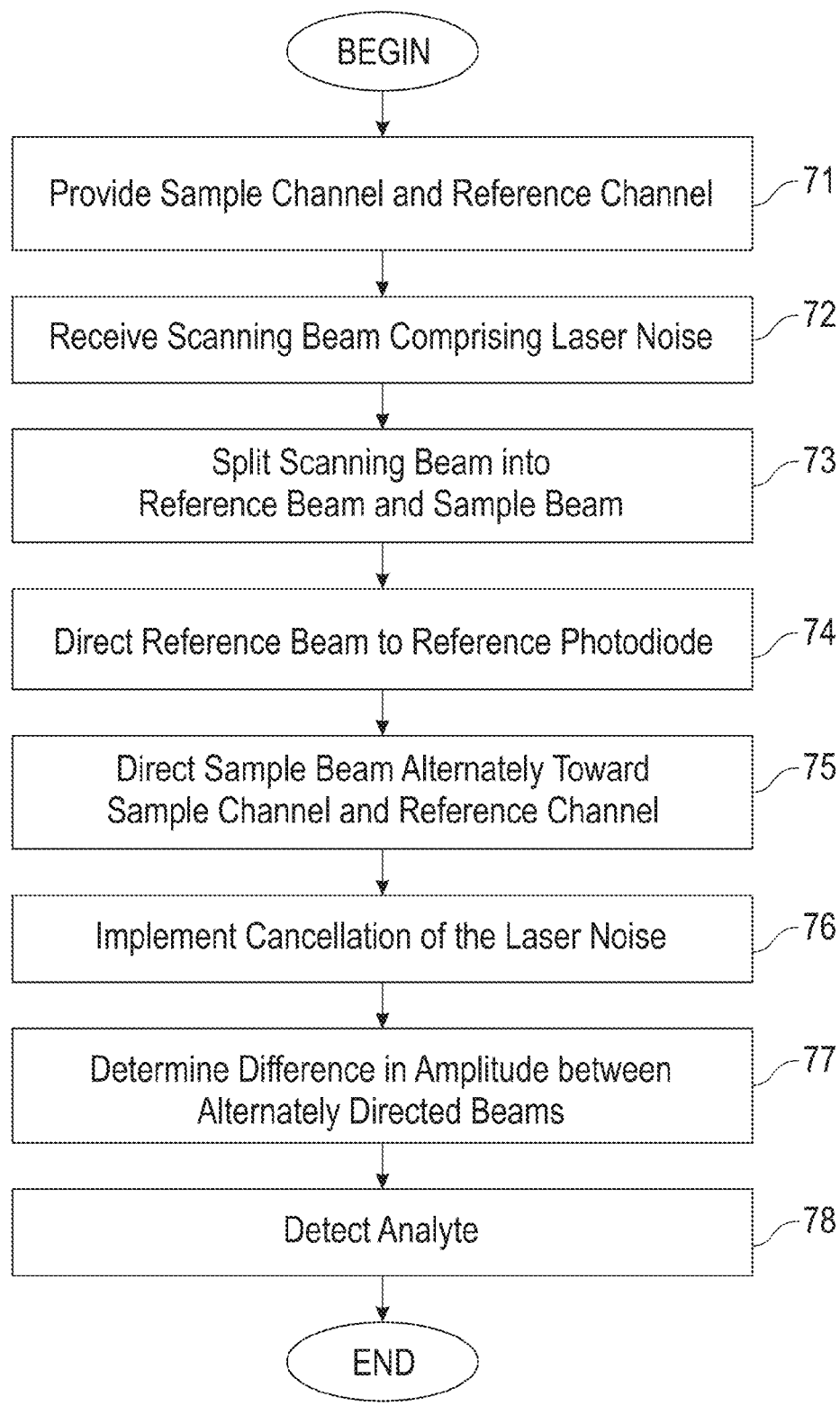
FIG. 5 is a flow chart depicting a method for detecting an analyte, in accordance with embodiments of the present invention.

FIG. 5 is a flow chart depicting a method for detecting an analyte, in accordance with embodiments of the present invention. The method of FIG. 5, which includes steps 71-78, encompasses both the first embodiment (FIGS. 3A, 3B) and the second embodiment (FIGS. 4A, 4B) of the present invention, described supra.

Step 71 provides a sample channel through which a sample fluid is flowing, a reference channel through which a reference fluid is flowing, and a metal layer in contact with the sample fluid and the reference fluid. The sample fluid comprises the reference fluid and the analyte. In one embodiment, the maximum molar concentration of analyte that may be in the reference fluid is about 50% of that in the sample fluid. In one embodiment, the reference fluid does not comprise the analyte. The reference channel and the sample channel are different channels.

In step 72, an optical system receives a scanning beam from a laser. The scanning beam comprises laser noise generated in the laser.

In step 73, the optical system splits the scanning beam into a reference beam and a sample beam. The reference beam comprises information pertaining to the laser noise.

In step 74, the optical system directs the reference beam to a reference photodetector causing the reference photodetector to send a resultant reference signal (e.g., a photocurrent or a wireless signal) to noise reduction electronics.

In step 75, the optical system directs the sample beam alternately toward the sample channel and the reference channel at a frequency of alternation (i.e., a modulation frequency). The directed sample beam is reflected from the metal layer such that surface plasmon resonance (SPR) is triggered in the metal layer. The reflected sample beam is directed to a sample photodetector causing the sample photodetector to send a resultant sample signal (e.g., a photocurrent or a wireless signal) to the noise reduction electronics.

In step 76, noise reduction electronics (i) implements a reduction of the laser noise by subtracting the laser noise component of the reference photocurrent from the sample photocurrent and (ii) generates an output signal comprising the sample signal after the laser noise component has been removed from the sample signal by being cancelled by the laser noise component of the reference signal.

Step 77 determines the difference in amplitude ($\Delta A$) between the alternately directed beams reflected at the metal layer alternately at the sample channel and the reference channel. In step 77, the output signal from the noise reduction electronics is processed by a lock-in amplifier that locks in (i.e., selects) the output signal from the noise reduction electronics having the modulation frequency determined by the scanner mirror. The lock-in amplifier determines, from processing different portions of cycles of the output signal from the noise reduction electronics, the difference in amplitude ($\Delta A$) between the alternately directed beams reflected at the metal layer. The difference in amplitude ($\Delta A$) is included in the output signal from the lock-in amplifier.

Step 78 determines the presence of analyte in the sample channel. In step 78, the output signal from the lock-in amplifier is sent to a computer system for further processing by a computer processor of the computer system, which includes determining the presence and amount of analyte in the fluid of the sample channel. In one embodiment, the amount of analyte present in the fluid of the sample channel may be determined from a calibration curve that plots the difference in amplitude ($\Delta A$) versus amount or concentration of analyte present. The calibration curve is specific to the analyte of interest being considered. In one embodiment, the maximum molar concentration of analyte that may be in the reference fluid is about 50% of that in the sample fluid.

Demonstration of Technique

Figure 6:
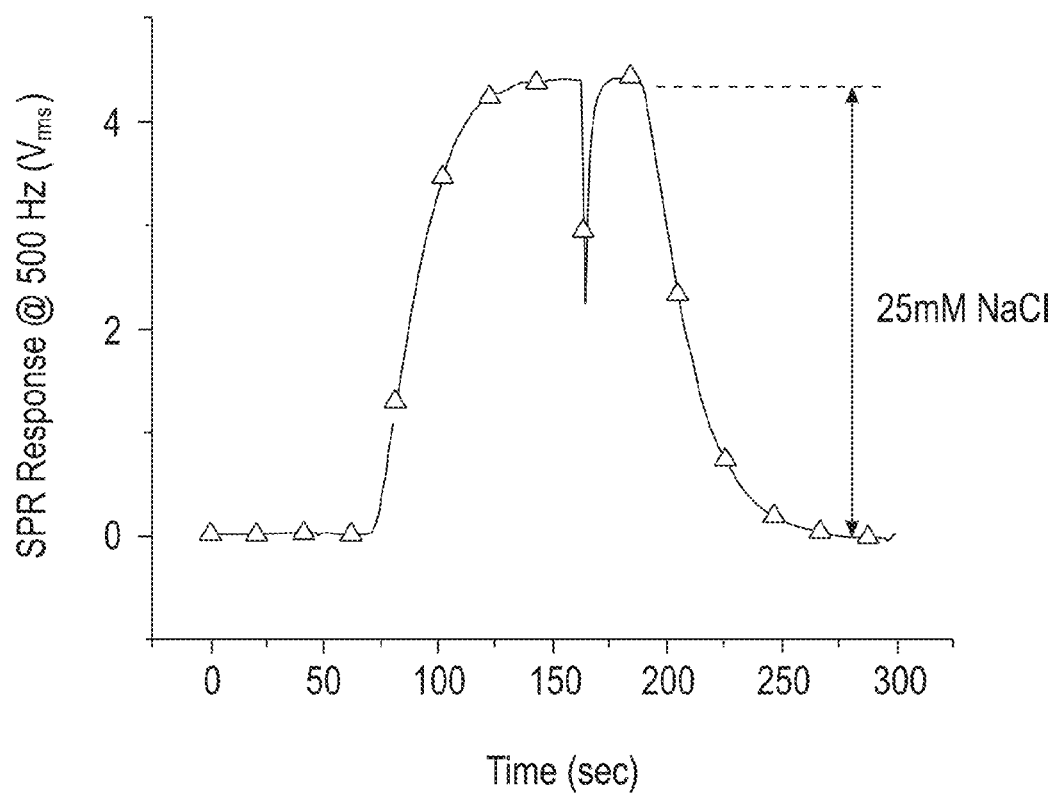
FIG. 6 depicts a graph of SPR response voltage versus time for a fluid whose refractive index is dynamically varied, in accordance with embodiments of the present invention.

FIG. 6 depicts a graph of SPR response voltage versus time for a fluid whose refractive index is dynamically varied, in accordance with embodiments of the present invention. FIG. 6 demonstrates the technique of the present invention by examining the difference in refractive index between two bulk solutions: deionized water and a 25 mM sodium chloride (NaCl) solution (the reference and sample channel, respectively). The sample beam is modulated at 500 Hz in accordance with the first embodiment based on FIG. 3A as described supra. The fluid is deionized water initially with an accompanying baseline response voltage of zero volts. At about 70 seconds, 25 mM NaCl is added to the fluid in the sample channel and the response voltage increases to about 4 volts at about 130 seconds when a steady state is reached, which reflects a change in refractive index ($\Delta n$) of the fluid due to the addition of NaCl. The sharp decrease in SPR response voltage at approximately 160 seconds is an experimental artifact due to a pressure difference introduced in the sample channel fluid by the addition of the 25 mM NaCl to the sample channel fluid. This pressure difference caused some of the fluid in the reference channel to move to the sample channel. This experimental artifact is not relevant to the present invention and therefore may be ignored. The NaCl is removed beginning at about 170 seconds which causes the response voltage to decrease continuously until the response voltage is the baseline value of zero volts at about 275 seconds, which reflects a return of the refractive index to its value for deionized water.

While surface plasmon resonance is typically used for monitoring interfacial changes, it is sensitive to any change within the evanescent wave of the surface plasmon which includes changes in the bulk refractive index. In this example, the addition of sodium chloride changes the bulk refractive index in the sample channel. The modulated signal between the reference and sample channels is fed into a lock-in amplifier which isolates the signal at the scanning frequency. A step change of known refractive index as shown in FIG. 6 is a simple method to determine the resolution of the system. The addition of sodium chloride to water, resulting in a 25 mM solution, changes the refractive index of the solution by ~2.4E-4 refractive index units (RIUs) for the wavelength of this experiment. The measured change in lock-in voltage output ($\Delta V$) is proportional to the known change in refractive index ($\Delta n$) due to the NaCl (see Equation (1) infra). Thus, the smallest refractive index change detectable by the apparatus ($n_{noise}$), measured in refractive index units, can be determined in accordance Equation (1) from the known refractive index change ($\Delta n$), the noise in the lock-in output ($V_{noise}$), and the change in lock-in voltage output ($\Delta V$).

$$n_{noise} = \Delta n * V_{noise} / \Delta V \quad (1)$$

Figure 7:
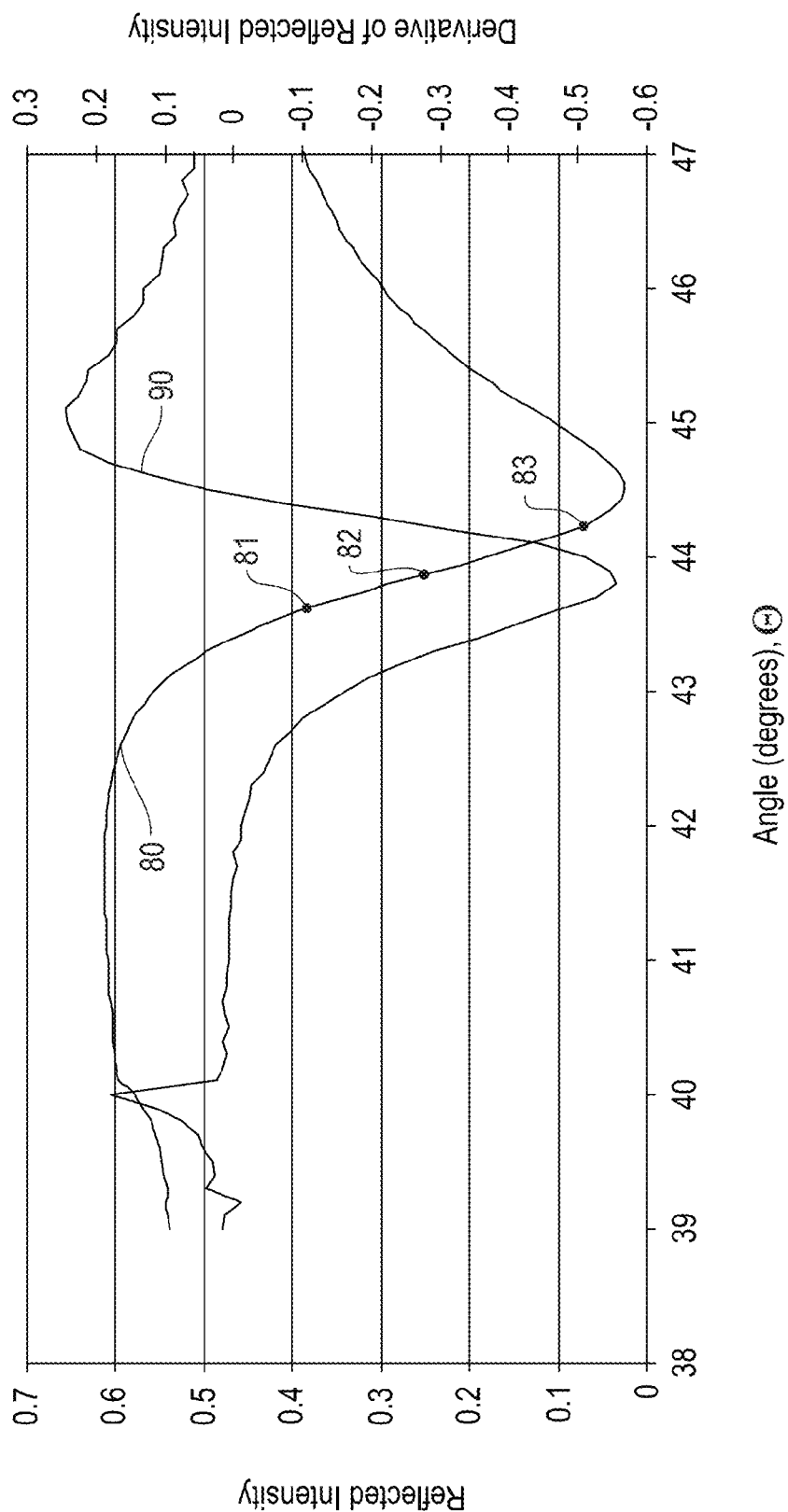
FIG. 7 is an exemplary SPR curve of reflected intensity versus angle of incidence of a scanning beam.

Equation (1) is valid for the linear regime of the SPR curve such as the SPR curve of FIG. 7 which is described infra. The refractive index noise ($n_{noise}$) for the system used in the experiment of FIG. 6 in its current state is ~2E-7, which is approximately one order of magnitude less than with commercially available systems.

The minimum achievable concentration of a specific biomarker is determined largely based on the interactions between the biomarker and the surface (e.g., a gold surface may be used). Typically, the surface is configured with a linker to selectively bind the biomarker of interest. For example, for a biomarker that is a specific protein, an antibody may be placed on the surface to serve as a linker for the specific protein because the antibody has a selective affinity for the particular protein. The lowest concentration that could be resolved is the minimum resolvable concentration for the specific biomarker under the conditions of the experiment, which corresponds to the signal change (due to $\Delta n$) being equal to the noise level.

Determining Sensitivity

FIG. 7 is an exemplary SPR curve 80 of reflected intensity versus angle $\Theta$ of incidence of a scanning beam. The scanning beam is an unmodulated laser beam (i.e., unmodulated in contrast with the modulation of sample beams 23 and 26 in FIGS. 3A and 3B, respectively) having a 830 nm wavelength. The laser beam is reflected off the sample surface (analogous to surface 49 in FIG. 2B), and the angle $\Theta$ is varied with respect to the surface normal to the sample surface. The angle $\Theta$ is the angle of incidence of the scanning beam 47 incident upon the surface 49 of the metal film 44 as depicted in FIG. 2B. The metal film is a gold film having a thickness of 48 nm. An adhesion layer of chromium of thickness 1.5 nm adheres the gold film to a SF11 (high refractive index glass) prism. The sample channel comprises MilliQ water, which is ultra pure water. The collected scanning beam exhibits a dip in reflected intensity which is associated with exciting surface plasmon polaritons in the metal film 44. The lock-in voltage output (V) is associated with the reflected intensity. FIG. 7 also depicts a derivative curve 90 which is the derivative of the reflected intensity 80. The SPR curve 80 in FIG. 7 has a linear regime, between points 81 and 83, which is approximately linear with an approximately constant slope and contains an inflection point 82 where the derivative curve 90 is minimized in FIG. 7. The derivative of the reflected intensity allows one to easily identify the inflection point where sensitivity of change in reflected intensity to angular change is maximized.

The minimum detection limit is typically defined as a signal-to-noise (SNR) ratio of 1. Therefore, knowledge of the noise level enables a determination of the sensitivity in refractive index units (RIUs). The minimum detectable RIU is given by Equation (2):

$$\text{RIU} = V_{noise}/(\text{slope of SPR linear regime}*\text{angular sensitivity to refractive index}) \quad (2)$$

wherein slope of SPR linear regime=$\delta V/\delta \Theta$ wherein $\delta V$ and $\delta \Theta$ denote a change in V and a change in $\Theta$, respectively at a specific angle $\Theta$ in the linear regime 81 of the SPR curve and, in one embodiment, may be taken at the inflection point 82 to maximize sensitivity. The ratio of angular sensitivity to refractive index is equal to $\Delta \Theta / \Delta \text{RIU}$. These values can be determined theoretically or experimentally using a calibration with known refractive index samples.

The minimum detectable concentration of a protein can be determined from the differential refractive index, dn/dc via Equation (3).

$$\text{Minimum detectable concentration} = \text{RIU}_{min} * dn/dc \quad (3)$$

CONCLUSION

The present invention provides a method, and an associated apparatus, based on surface plasmon resonance to achieve ultrasensitive interfacial detection of gas and solution-phase biological and chemical analytes. Increased sensitivity is achieved by signal modulation with active electronic noise suppression. The first embodiment utilizes the barrierless construct accomplished with the incorporation of a flow cell. This allows a single laser source to transverse between the two channels without signal contamination in the frequency domain that would increase noise. The second embodiment utilizes polarization modulation to rapidly alternate a laser beam between two flow channels. Further, each embodiment operates in a self-referencing mode to eliminate the undesired contribution of non-specific interfacial adsorption (e.g., serum proteins) making the apparatus particularly useful for ultrasensitive measurements in the presence of complex media (e.g., blood).

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A device, comprising:
   sample and reference channels through which first and second solutions flow, respectively, wherein the first solution includes an analyte of interest, the channels having a metal film in contact with the first and second solutions, a surface of the metal film configured with a linker to selectively bind the analyte to the surface of the metal film;
   a light source whose output is modulated by an optical system, so that light is directed from the optical system alternately towards the sample and reference channels, wherein surface plasmons within the metal film are created;
   a first photodetector that monitors the strength of the output from the light source;
   a second photodetector that collects optical signals reflected from the metal film;
   electronics that monitors output from both the first and the second photodetectors, thereby detecting a noise-compensated difference in signals from the two channels; and
   a computer processor performing an analysis of the noise-compensated difference and determining from the analysis that the analyte is present in the first solution.

2. The device of claim 1, wherein:
   the optical system includes a scanner mirror whose motion directs the light from the optical system alternately towards the sample and reference channels; and the sample and reference channels are contained within a single flow cell, the first and second solutions being essentially separated from each other.

3. The device of claim 1, wherein the optical system includes a photoelastic modulator and a polarizing beam displacer, wherein the photoelastic modulator changes the polarization of light traversing the optical system to alternate the polarization between different states of polarized light.

4. The device of claim 3, wherein the sample and reference channels are contained within a single flow cell such that the first and second solutions are essentially separated from each other.

5. The device of claim 3, wherein the sample and reference channels are physically separated from each other.

6. An apparatus for detecting an analyte, said apparatus comprising:
a reference channel through which a reference fluid is flowing;
a sample channel through which a sample fluid is flowing, said sample fluid comprising the reference fluid and the analyte, said reference fluid comprising a molar concentration of the analyte that is no more than 50% of the analyte that is in the sample fluid, said reference channel and said sample channel being different channels;
a metal layer in contact with the sample fluid and the reference fluid, a surface of the metal layer configured with a linker to selectively bind the analyte to the surface of the metal layer;
an optical system;
a reference photodetector coupled to the optical system;
a sample photodetector;
noise reduction electronics coupled to the reference photodetector and the sample photodetector;
a lock-in amplifier coupled to the noise reduction electronics; and
a computer processor coupled to the lock-in amplifier;
said optical system configured to receive a scanning beam from a laser, said scanning beam comprising laser noise generated in the laser;
said optical system configured to split the scanning beam into a reference beam and a sample beam, said sample beam and said reference beam each comprising the laser noise;
said optical system configured to direct the reference beam to the reference photodetector causing the reference photodetector to send a resultant reference signal containing the laser noise to the noise reduction electronics;
said optical system configured to direct the sample beam alternately toward the sample channel and the reference channel under conditions where surface plasmon resonance (SPR) occurs in the metal layer, said directed sample beam being alternately reflected from the surface of the metal layer at the sample and reference channels;
said optical system configured to direct the reflected sample beam to the sample photodetector causing the sample photodetector to send a resultant sample signal containing the laser noise to the noise reduction electronics;
said noise reduction electronics configured to (i) implement a reduction of the laser noise from the sample signal via utilization of the reference signal and (ii) generate an output signal comprising the sample signal after the laser noise has been removed from the sample signal;
said lock-in amplifier configured to (i) lock in to the output signal from the noise reduction electronics and (ii) determine, from processing different portions of cycles of the output signal from the noise reduction electronics, a difference in amplitude ($\Delta A$) between the alternately directed beams reflected at the metal layer, said $\Delta A$ being determined after the laser noise has been cancelled from the sample signal;
said computer processor configured to perform an analysis of the difference in amplitude ($\Delta A$) determined by the lock-in amplifier and to determine from the analysis that the analyte is present in the sample fluid flowing in the sample channel.

7. The apparatus of claim 6,
wherein the optical system comprises a scanner mirror,
wherein the optical system is configured to direct the sample beam to strike the scanner mirror while the scanner mirror is engaged in rotational motion, and
wherein the sample channel and the reference channel are contained within a single barrierless fluidic flow cell.

8. The apparatus of claim 6,
wherein the optical system is configured to modulate the sample beam between two polarizations by alternating the two polarizations at a frequency of alternation; and is configured to separate the two polarizations from each other by a spatial distance.

9. The apparatus of claim 8,
wherein the optical system comprises a photoelastic modulator and a polarizing beam displacer;
wherein the photoelastic modulator modulates the sample beam between circularly polarized light and P polarized light; and said optical system changes the circularly polarized light to S polarized light; and
wherein the optical system is configured to use the polarizing beam displacer to separate the S polarized light and the P polarized light from each other by the spatial distance.

10. The apparatus of claim 9,
wherein the optical system comprises a half-wave plate and a linear polarizer;
wherein the optical system is configured to use the half-wave plate to rotate the S polarized light and the P polarized light by 45 degrees, after the S polarized light and the P polarized light have been separated from each other by the spatial distance; and
wherein the optical system is configured to use the linear polarizer to remove the S polarized light which causes the sample beam to have a constant overall intensity that alternates between two positions in space respectively corresponding to where the sample channel and the reference channel are located, after the half-wave plate has been used to rotate the S polarized light and the P polarized light by 45 degrees.

11. The apparatus of claim 9, wherein the optical system comprises a quarter wave plate that changes the circularly polarized light to S polarized light.

12. The apparatus of claim 8, wherein the sample channel and the reference channel are contained within a single barrierless fluidic flow cell.

13. The apparatus of claim 8, wherein the sample channel and the reference channel are separated from each other by a physical barrier.

14. The apparatus of claim 6, wherein the reference fluid does not comprise the analyte.

15. The apparatus of claim 6, wherein the reference fluid comprises a molar concentration of the analyte that is no more than 50% of the molar concentration of the analyte that is in the sample fluid.

16. The apparatus of claim 6, comprising a spherical mirror, wherein the optical system directs the alternately reflected sample beam toward the spherical mirror, wherein the spherical mirror reflects the alternately reflected sample beam into respective paths toward the sample and reference photodetectors, and wherein the respective paths are parallel to each other.

17. The apparatus of claim 6, wherein at least one photodetector of the reference photodetector and the sample photodetector is a photodiode.

18. The apparatus of claim 6, wherein at least one photodetector of the reference photodetector and the sample photodetector is a wireless device.

19. A method of forming the apparatus of claim 6, said method comprising:
configuring the surface of the metal layer with the linker to selectively bind the analyte to the surface of the metal layer;
positioning the sample fluid and the reference fluid in contact with the configured surface of the metal layer;
coupling the reference photodetector to the optical system;
coupling the noise reduction electronics to the reference photodetector and the sample photodetector;
coupling the lock-in amplifier to the noise reduction electronics; and
coupling the computer processor to the lock-in amplifier.

20. A method of detecting a substance through use of the apparatus of claim 6, said method comprising:
said optical system receiving the scanning beam from the laser;
said optical system splitting the scanning beam into the reference beam and the sample beam;
said optical system directing the reference beam to the reference photodetector causing the reference photodetector to send the resultant reference signal to the noise reduction electronics;
said optical system directing the sample beam alternately toward the sample channel and the reference channel at the frequency of alternation, said directed sample beam being reflected from the metal layer such that surface SPR is triggered in the metal layer, said reflected sample beam being directed to the sample photodetector causing the sample photodetector to send the resultant sample signal to the noise reduction electronics;
said noise reduction electronics (i) implementing the reduction of the laser noise from the sample signal via utilization of the reference signal and (ii) generating an output signal comprising the sample signal after said implementing the reduction of the laser noise;
said lock-in amplifier (i) locking in to the output signal from the noise reduction electronics and (ii) determining, from processing different portions of cycles of the output signal from the noise reduction electronics, said difference in amplitude ($\Delta A$); and
said computer processor performing an analysis of the difference in amplitude ($\Delta A$) and determining from the analysis that the substance is present in the sample fluid flowing in the sample channel, said substance being the analyte.

* * * * *